(12) United States Patent
Klokkers

(10) Patent No.: US 6,204,255 B1
(45) Date of Patent: Mar. 20, 2001

(54) SOLID, NON-DELIQUESCENT FORMULATIONS OF SODIUM VALPROATE

(75) Inventor: Karin Klokkers, Holzkirchen (DE)

(73) Assignee: Hexal AG, Holzkirchen (DE)

(*) Notice: Subject to any disclaimer, the term of this patent is extended or adjusted under 35 U.S.C. 154(b) by 0 days.

(21) Appl. No.: 09/180,821

(22) PCT Filed: Mar. 11, 1998

(86) PCT No.: PCT/EP98/01404
§ 371 Date: May 24, 1999
§ 102(e) Date: May 24, 1999

(87) PCT Pub. No.: WO98/40060
PCT Pub. Date: Sep. 17, 1998

(51) Int. Cl.$^7$ .......................... A61K 31/715; A61K 31/19
(52) U.S. Cl. ........................... 514/58; 514/557; 514/964; 514/965; 424/468

(58) Field of Search ............................ 514/58, 557, 964, 514/965; 424/468

(56) References Cited

U.S. PATENT DOCUMENTS 4,834,985 * 5/1989 Elger et al. .......................... 424/488
5,688,510 * 11/1997 Nakamichi et al. .............. 424/195.1

OTHER PUBLICATIONS

Cerestar USA (product literature for Cavitron Cyclodextrins), 1996.*

* cited by examiner

Primary Examiner—Howard C. Lee
(74) Attorney, Agent, or Firm—Pitney, Hardin, Kipp & Szuch, LLP

(57) ABSTRACT

Non-deliquescent formulation comprising or consisting of sodium valproate and cyclodextrin having a molar ratio of sodium valproate to cyclodextrin within the range of from 1:0.01 to 1:0.09.

14 Claims, No Drawings

SOLID, NON-DELIQUESCENT FORMULATIONS OF SODIUM VALPROATE

The present invention relates to solid pharmaceutical formulations of non-deliquescent compositions of sodium valproate with cyclodextrins. These formulations are characterized by a high valproate content and by having improved technological properties like enhanced flowing, better tablettability and higher stability to moisture. The invention further describes improved granulation and tabletting processes.

BACKGROUND OF THE INVENTION

Valproate is a broad spectrum antiepileptic and anticonvulsive agent. Valproic acid is liquid at room temperature and thus not suitable for manufacturing of solid dosage forms, e.g., tablets for oral administration. Sodium valproate is solid, but an extremely hygroscopic, deliquescent substance. It absorbs water from the atmosphere already during tabletting, resulting in problems of tablet production, like sticking to the punches.

A valproic cid-sodium valproate 1:1 complex (divalproex sodium) is described in U.S. Pat. No. 5,212,326 and WO 96/23491. It is a solid at room temperature and is described to be nonhygroscopic.

To eliminate the extreme tendency to deliquescence, various methods have been recommended. One possibility is the hydrophobic coating of the tablets (Yamatogi, Yasuko; Yokhinaga, Harimi; Oka, Eiji; Ohtahara, Shunsuke; Yamashita, Syoichi; Furuno, Katsushi; Gomita, Yutaka, Psychiatry Clin. Neurosci. (1995), 49(3), S245–S247 (Chem. Abstr.:23:217657)). Another way is to use the prodrug of valproic acid, valpromide, a primary amide of valproic acid, which is a solid, neutral, non-hygroscopic material having several pharmaceutical advantages over valproic acid or sodium valproate (Bialer, Meir, Trends, Med. Chem. '90, Proc. Int. Symp. Med, Chem., 11$^{th}$ (1992), 337–81. Editor (s): Sarel, Shalom; Mechoulam, Raphael; Agranat, Israel. Publisher:Blackwell, Oxford, UK.)

It has been found by the inventors that granulation of sodium valproate leads to a water content of more than 2%. This results in extreme technical problems of further processing the granules, e.g., in order to produce the compression mass and to tablet the mass. Problems are sticking to the punches and an increase of rejection force of the lower punch, stopping the tabletting machine. A too dry compression mass leads to capping of the tablets while sticking is reduced. That means when sodium valproate is granulated with, e.g.,. lactose, the absolute humidity of the compression mass should not be above 2% to be successfully tabletted after granulation. To enable production, usually high technical efforts have to be made and expensive equipment is necessary, like air conditioning to low relative moisture.

It is further known that inclusion complex formation with cyclodextrins can suppress the deliquescence of sodium valproate (JP 56133236). The effective molar ratio of sodium valproate/cyclodextrin complex is claimed to be in the range of 1:0.1 to 1:2. This is, however, technically not feasible because the daily dose of valproate is 2 g, i.e., to this dose 1.4 g to 28 g β-cyclodextrin would be necessary, which—taking into account the further inevitable tablet ingredients, like binding, gliding, disintegrating additives would result in unacceptable large tablets.

The object of the invention is to provide solid formulations of sodium valproate with increased stability to deliquescence, to pharmaceutical formulations with high sodium valproate content and to processes with improved technical handling features to prepare the same.

According to the present invention, it has surprisingly been found that cyclodextrins are effective in decreasing the deliquescence of sodium valproate, by forming a composition of sodium valproate with cyclodextrin at a molar ratio of 1:0.01 to 1:0.09, preferably at a molar ratio of 1:0.02 to 1:0.05. In this case, only one cyclodextlin molecule to about 25–50 valproate molecules is necessary to prevent the deliquescence of the drug. This amount of cyclodextrin is not enough to clathrate the drug. The inclusion complex formation is practically not detectable, and the cyclodextrin behaves as an unusual antideliquescence carrier in the solid dispersion.

According to the present invention, the first three members of cyclodextrin homologues, that is α-, β-or y-cyclodextrin can be used.

In the embodiments of the present invention, the solvent evaporation method is applied, preferably with water. The use of any other solvent of sodium valproate (e.g., ethanol, dimethyl sulfoxide) is limited because particular attention has to be devoted to the removal of the residual solvent that may be toxic and environmental polluting at the production. Generally, their presence is not tolerated in the finished product. As cyclodextrins form inclusion complexes with most of these solvents, the removal of last traces might be difficult.

The solid dispersion according to the invention can be prepared by the following methods:

Solution method:

Sodium valproate and a water soluble cyclodextrin are dissolved in water. The solution is stirred thoroughly and water is removed by evaporation or freeze drying or spray drying to obtain the solid dispersion.

Suspension method:

Sodium valproate is dissolved in water and β-cyclodextrin is suspended in the valproate solution. The solid dispersion is obtained by freeze drying or spray drying.

Kneading method:

The components are well mixed, then wetted with water, kneaded thoroughly at 0–80° C. and dried in an oven at 40–110° C. It has further been found that the solid dispersion of the invention has improved technological properties, showing enhanced flowability, tabletability and stability to moisture. Especially with respect to the stability to moisture, the solid dispersion shows features that enable a granulation and tabletting process with an absolute moisture content of about 3–5%.

The advantage of the present invention is that using cyclodextrins, in far less than the stoichiometric ratio (i.e., without formation of inclusion complex) the obtained product is non-deliquescent and has improved handling and processing characteristics. Sodium valproate itself can only be tabletted, if air conditioning to low relative humidity and/or anti adhesive coating of the punches and other expensive and non standard measures during routine tablet production are applied, because of the poor flowing and high sticking to the tabletting machine of the tabletting masses with a high concentration of the active ingredient. Using as low as 10–40 weight percent β-cyclodextrin (equivalent to 1:0.01 to 1:0.09 drug to cyclodextrin molar ratio) the product has improved flowing and ejection properties, even in the presence of 3–5% of loss drying of the compression mass.

In contrast to complexes formed by equimolar amounts of sodium valproate and cyclodextrin dosage forms can be prepared having a sodium valproate content of 50 to 90% by weight. Usually single dose tablets contain 300 to 600 mg sodium valproate. According to the invention, tablets having a total weight of 500 to 950 mg can be prepared. Moreover, the solid dispersion is also suitable for direct tabletting.

The granulation process can be done by standard methods, e.g., fluid bed or wet granulation. The solid dispersion will granulate together with usual excipients like polyvinylpyrrolidone, silicon dioxide, cellulose esters, cyclodextrins, etc. The granulate will be further processed to tablets by employing usual techniques, and may also contain cyclodextrin as further excipient. The tablets may further be enteric coated.

The solid dispersion can further be used for the preparation of sustained release compositions. The sustained release compositions can be obtained with hydrogel matrices like HPMC, alginic acid, and/or salts thereof, and/or polyacrylates such as Eudragit® and may, in addition, contain a pharmaceutically acceptable organic acid such as citric acid, tartaric acid or succinic acid or salts of these acids.

The following examples are presented to further illustrate the present invention.

EXAMPLE 1

166 g (1 mole) sodium valproate and 60 g (moisture content 14%, 0.045 mole) β-cyclodextrin are blended and 30 mL water is added. The ingredients are thoroughly kneaded in a laboratory mortar. The cream-like product is dried at 60° C. under vacuum. 202.3 g product is obtained by grinding. (The weight ratio of the drug to cyclodextrin is 1:0.31.) One gram of the dried product is placed into a Petri dish and stored for 24 hours at 40° C. under 75% relative humidity. The moisture absorption measured by the weight-increase was found to be 48%, compared to 70% of sodium valproate itself. After storage, the product looks wet but not liquified, while sodium valproate itself or the product obtained, in a similar way with lactose instead of β-cyclodextrin, are liquified.

EXAMPLE 2

166 g (1 mole) sodium valproate and 120 g (moisture content 14%, 0.09 mole) β-cyclodextrin are blended and 60 mL water is added. The ingredients are thoroughly kneaded and the product is obtained by drying and grinding as described in Example 1. (The weight ratio of the drug to cyclodextrin is 1:0.62) The moisture absorption after 24 hour storage at 40° C. under 75% relative humidity was found to be 36%, compared to 70% and 47% of sodium valproate itself and of the product obtained in a similar way with lactose instead of β-cyclodextrin, respectively. The latter two were liquified.

EXAMPLE 3

166 g (1 mole) sodium valproate and 90 g (moisture content<5%, 0.09 mole) a α-cyclodextrin are blended and 20 mL water is added. The ingredients are thoroughly kneaded, and the product is obtained by drying and grinding as described in Example 1. The moisture absorption after 24 hour storage at 40° C. under 75% relative humidity was found to be 43%, compared to 70% and 47% of sodium valproate itself and of the product obtained in a similar way with lactose instead of a α-cyclodextrin, respectively. The latter two were liquified.

EXAMPLE 4

166 g (1 mole) sodium valproate and 120 g (moisture content<5%, 0.09 mole) γ-cyclodextrin are blended and 20 mL water is added. The ingredients are thoroughly kneaded and the product is obtained by drying and grinding as described in Example 1. The moisture absorption after 24 hour storage at 40° C. under 75% relative humidity was found to be 30%, compared to 70% and 47% of sodium valproate itself and of the product obtained in a similar way with lactose instead of γ-cyclodextrin, respectively.

EXAMPLE 5

166 g (1 mole) sodium valproate and 60 g (moisture content 14%, 0.045 mole) β-cyclodextrin are blended and 300 mL water is added. The ingredients are thoroughly mixed. The 212 g product is obtained by freeze drying. The moisture absorption after 24 hour storage at 40° C. under 75% relative humidity was found to be 45%, compared to 70% and 56% of sodium valproate itself and of the product obtained in a similar way with lactose instead of β-cyclodextrin, respectively.

EXAMPLE 6

Tablets of 10 mm diameter and 0.5 g weight are compressed from the products obtained by Example 1 by direct compression without further tabletting ingredients. The flowing properties as well as the compressibility of the product were much better than those of the physical mixture of sodium valproate and β-cyclodextrin. The tablets were stored at 40° C. under 75% relative humidity. The moisture absorption of tablets of sodium valproate/β-cyclodextrin kneaded product, physical mixture and of the product obtained by kneading with lactose instead of β-cyclodextrin after 24 hour storage was found to be 32.9, 36.3 and 52%, respectively, the last one was liquified.

EXAMPLE 7

3 kg sodium valproate, 0.834 kg β-cyclodextrin and 0.066 kg Kollidon were granulated in a fluid bed granulator. Further, the granulate was mixed with 0,32 kg microcrystalline cellulose, 0.65 kg lactose, 0.025 kg silicium dioxide and magnesium stearate and compressed to tablets. The tablets were enteric coated.

EXAMPLE 8

3 kg sodium valproate, 0.4 kg β-cyclodextrin and 0.07 kg Kollidon were granulated as described above. The granulate was mixed with 0.32 kg microcrystalline cellulose, 0,3 kg lactose, 0.025 kg silicium dioxide, 0.5 kg β-cyclodextrin and magnesium stearate and compressed to tablets. The tablets were then enteric coated.

EXAMPLE 9

3 kg sodium valproate, 1 kg β-cyclodextrin, 2 kg Metolose 90 SM 100000, 1,15 kg anhydracitric acid and 0,4 kg Kollidon were granulated in a fluid bed granulator. The granulate will be compressed together with magnesium stearate and finally film coated.

What is claimed is:

1. A non-deliquescent formulation comprising of sodium valproate and cyclodextrin having a molar ratio of sodium valproate to cyclodextrin within the range of from 1:0.01 to 1:0.09.

2. The formulation according to claim 1, wherein the molar ratio of sodium valproate to cyclodextrin is within the range of from 1:0.02 to 1:0.05.

3. The formulation according to claim 1 wherein the cyclodextrin is α-cyclodextrin, β-cyclodextrin or γ-cyclodextrin.

4. The formulation according to claim 1 further comprising a pharmaceutically acceptable auxiliary agent.

5. The process according to claim 4, wherein the solution is brought to dryness by evaporation, vacuum drying, freeze drying, lyophilisation or spray drying.

6. A pharmaceutical preparation comprising the formulation of claim 1 and a pharmaceutically acceptable excipient.

7. The pharmaceutical preparation of claim 6 wherein the physical form of the preparation is selected from the group consisting of powders, tablets, granulates and capsules and wherein tablet or granular forms of the preparation have an absolute moisture content of 3 to 5% by weight.

8. The pharmaceutical preparation according to claim 6 having a sodium valproate content of 50 to 90% by weight.

9. The pharmaceutical preparation according to claim 6 wherein the preparation is in tablet form.

10. The pharmaceutical preparation according to claim 9, wherein the preparation is a sustained release preparation.

11. The pharmaceutical preparation according to claim 6 containing a therapeutically effective organic acid and/or a salt thereof.

12. A process for preparing a formulation according to claim 1, involving the steps of:

(a) mixing sodium valproate and cyclodextrin in the presence of water and/or alcohol;

(b) forming an aqueous and/or alcoholic solution; and (c) drying the solution.

13. A process for preparing a formulation according to claim 1, involving the steps of:

(a) mixing sodium valproate and cyclodextrin in the presence of water and/or alcohol;

(b) forming an aqueous and/or alcoholic dispersion of the cyclodextrin or of both components; and (c) drying the dispersion.

14. The process according to claim 13, wherein the dispersion is brought to dryness by evaporation, vacuum drying, freeze drying, lyophilisation or spray drying.

* * * * *

UNITED STATES PATENT AND TRADEMARK OFFICE
CERTIFICATE OF CORRECTION

PATENT NO.    : 6,204,255 B1  
DATED         : March 20, 2001  
INVENTOR(S)   : Karin Klokkers It is certified that error appears in the above-identified patent and that said Letters Patent is hereby corrected as shown below:

<u>Title page,</u>  
Insert the following:  
    -- [30], Foreign Application Priority Data  
Mar. 11, 1997   HU     Hungary ……………………….. 7337/97 --

Signed and Sealed this

Ninth Day of July, 2002

*Attest:*

JAMES E. ROGAN  
*Attesting Officer*    *Director of the United States Patent and Trademark Office*